United States Patent [19]

Reers et al.

[11] Patent Number: 4,959,357
[45] Date of Patent: Sep. 25, 1990

[54] PHOSPHOLIPASE A2 INHIBITOR

[75] Inventors: Martin Reers; Douglas R. Pfeiffer, both of Austin, Minn.

[73] Assignee: Regents of the University of Minnesota, Minneapolis, Mich.

[21] Appl. No.: 769,154

[22] Filed: Aug. 23, 1985

[51] Int. Cl.$^5$ .......................... A61K 31/66; C07F 1/11
[52] U.S. Cl. ...................... 514/103; 260/403; 514/928
[58] Field of Search ............... 260/403, 928; 558/160; 514/102, 103

[56] References Cited

U.S. PATENT DOCUMENTS 3,962,292  6/1976  Szuhaj et al. ................. 260/403

OTHER PUBLICATIONS

Eaton et al., *J. Org. Chem.*, vol. 37, No. 12, (1972), pp. 1947–1950.
Torregrossa et al., Chemical Abstracts 87: 113704x, (1977).
Cable et al., Chemical Abstracts 89: 1991y, (1978).
R. E. Torregrossa et al., J. of Bact., 131(2) (1977), 493-498.
M. B. Cable et al., Proc. Natl Acad. Sci., 75(3) (1978), 1227-1231.

*Primary Examiner*—Carolyn S. Elmore
*Attorney, Agent, or Firm*—Merchant, Gould, Smith, Edell, Welter & Schmidt

[57] ABSTRACT

Potent, specific inhibitors of phospholipase $A_2$ are disclosed which are compounds of the formula:

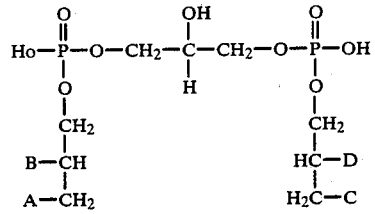

wherein A is $R_1CO_2$ or OH, B is $R_2CO_2$ or OH, D is $R_3CO_2$ or OH and C is $R_4CO_2$; and wherein $R_1$, $R_2$, and $R_3$ and $R_4$ are each $C_{10}$–$C_{30}$ alkyl groups comprising from about 0–3 double bonds.

8 Claims, 4 Drawing Sheets

PHOSPHOLIPASE A2 INHIBITOR

This invention was made with the assistance of Grant No. HL08214, awarded by the National Institute of Health, and the Hormel Foundation. The Government has certain rights invention.

BACKGROUND OF THE INVENTION

Mitochondria from many sources possess phospholipase $A_2$ activity associated with both their inner and outer membranes. The physiological functions of this enzyme or enzyme group has not been established with certainty although several reasonable, potential functions can be hypothesized. These include the possible involvement of mitochondrial phospholipase $A_2$ in regulating membrane permeability and therefore such processes as calcium ion ($Ca^{+2}$) accumulation and release, the efficiency of ATP synthesis, and cellular thermogenesis. Other possible functions of this enzyme include the modification of phospholipid acyl group composition, the initiation phospholipid degradation, and the liberation arachidonic acid to initiate the "arachidonic acid cascade," which involves the synthesis of prostaglandins and related compounds. While generally the products of the cascade are beneficial, in certain disease processes and other conditions the production of prostaglandins and similar products induces deleterious consequences such as inflammation (see paper by N. A. Plummer et al., abstracted in Journal of Investigative Dermatology, Vol. 68, No. 4, p. 246 (1977)); erythema; platelet aggregation (B. B. Vargaftig, J. Pharm. Pharmacol., Vol. 29, p. 222-228 (1977)); and the release of SRS-A (slow reacting substance-anaphylaxis), a known mediator of allergic responses. The inhibition of phospholipase $A_2$ can prevent these and similar conditions mediated by the action of this enzyme.

In cells which are injured by ischemia, chemical, mechanical or other means, the mitochondria develop impaired functional capacities and the extent of these metabolic lesions can be pivotal factors in the recovery or death of the injured cell. Persistent activation of mitochondrial phospholipase $A_2$, arising because of loss of cellular $Ca^{2+}$ homeostasis, is a probable dominant mechanism by which mitochondrial damage develops. There is also reason to suspect that phospholipase $A_2$-dependent loss of mitochondrial function may play an important role in the etiology of several significant human diseases including Reye's syndrome, muscle wasting diseases and malignant hyperthermia.

Thus a need exists for compounds which act to inhibit the activity of phospholipase $A_2$. Useful inhibitory compounds would be specific, potent and nontoxic. The inhibitors could be employed to control mitochondrial damage and damage to other membranous structures in injured or diseased mammalian tissue and thereby limit permanent damage and improve cellular survival. Hereinafter the deleterious effects and pathologies dependent entirely or in part upon phospholipase $A_2$ activity will be referred to as phospholipase $A_2$ mediated conditions (PMC).

SUMMARY OF THE INVENTION

The present inventions are directed to compounds which are highly active to inhibit phospholipase A in vivo or in vitro. Thus, such compounds would be expected to generally be useful to treat or prevent PMC in mammals, e.g. domesticated animals and humans. The compounds of the present invention can be generally represented by formula I:

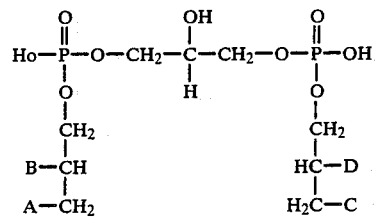

wherein A is $R_1CO_2$ or OH, B is $R_2CO_2$ or OH D is $R_3CO_2$ or OH and C is $R_4CO_2$; wherein each of $R_1$, $R_2$, $R_3$ and $R_4$ is a $C_{10}$–$C_{30}$ alkyl group, preferably a $C_{12}$–$C_{22}$ n-alkyl group comprising from 0-3 double bonds.

Therefore, the A-D acyl groups, are preferably derived from saturated or unsaturated fatty acids such as an alkanoic, alkenoic, dienoic or trienoic acids. Such acids include lauric, oleic, palmitic, linoleic, linolenic, stearic, eleastearic, palmitic, palmitoleic, petroselenic, vaccenic, erucic acid and the like and mixtures thereof. Preferably, one of A or B is OH, or B and D are OH.

Formally, the compounds of the present invention are the partial hydrolysis products of a known, naturally occurring compound, cardiolipin. In its "pure" form, cardiolipin can be represented by formula I wherein A, B, C and D are each $RCO_2$ moieties, wherein $RCO_2$ is derived from a variety of saturated and unsaturated fatty acids, such as those described hereinabove. The preferred compositions of the present invention can be isolated from mammalian mitochondria, and so are probably derived from in vivo hydrolysis of cardiolipin. For example, the compound designated as monolysocardiolipin can be represented by formula I wherein A is $R_1CO_2$, C is $R_4CO_2$, D is $R_3CO_2$, and B is OH. Iso-monolysocardiolipin can be represented by formula I wherein B is $R_2CO_2$, C is $R_4CO_2$, D is $R_3CO_2$ and A is OH, while in dilysocardiolipin A is $R_1CO_2$, D is $R_3CO_2$ and B and C are OH.

Although small amounts of certain of these compounds have been formed by hydrolysis of cardiolipin (J. Biol. Chem., 249, 3423 (1974)), the present invention is directed to pharmaceutically effective dosage forms containing mono- and dilysocardiolipin and the analogs thereof within the scope of formula I, in substantially pure form. Therefore, the present invention is directed to phospholipase $A_2$ inhibitors which can be structurally defined with precision, e.g., wherein the structure of each acyl ($RCO_2$) group is known; and to phospholipase $A_2$ inhibitors wherein the $RCO_2$ groups are varied to the extent that the active composition is a mixture of compounds falling within the scope of formula I.

For example, the composition designated monolysocardiolipin is made up of compounds of formula I which yield at least twelve different fatty acid residues upon hydrolysis (see Table II, below). On the other hand, mono- or dilysocardiolipins of homogeneous composition may be readily prepared by selectively protecting, acylating and deprotecting the five hydroxyl moieties present on the compound of formula I wherein A=B=C=D= hydroxy. Methods for the selective preparation of esters and for the selective protection and deprotection of OH groups are well-known in the art. See, e.g., Compendium of Organic Synthetic Methods, I. T. Harrison et al., eds., Wiley-Interscience, N.Y. (1971) and J. Org. Chem. 37 1947 (1972).

DETAILED DESCRIPTION OF THE INVENTION

During the purification of phospholipase $A_2$ from rat liver mitochondria, as described by Aarsman et al. in Biochem. Biophys. Acta., 792, 363 (1984), solubilization of the enzyme by production of an acetone powder extract was found to yield only about five percent of the starting enzyme activity. However, subjecting the extract to gel filtration chromatography increased the recovered activity by about ten-fold, as summarized on Table I, below. These findings suggested to us that an inhibitor, which was removed by gel filtration, was present in the acetone powder extract.

TABLE I
PHOSPHOLIPASE $A_2$ PURIFICATION SUMMARY

| Fraction | Protein Recovery mg | Activity Recovery nmol/min | Specific Activity mU/mg | Fold Purification |
|---|---|---|---|---|
| Mitochondria | 1699.0 | 1607 | 1.0 | 1 |
| Acetone Powder Extract | 1310.0 | 78 | 0.1 | 0.1 |
| AcA54 Chromatography Fractions | 1.8 | 880 | 767 | 808 |
| Ultrafiltrate | 1.7 | 234 | 136 | 144 |
| Dialysate | 1.6 | 165 | 109 | 114 |
| Affinity Column | | | | |
| Fracs. 22-28 | 0.03 | 131 | 4503 | 4740 |
| Frac. 23 | 0.01 | 39 | 7923 | 8340 |

Examination of gel filtration column fractions revealed phospholipase $A_2$ inhibitor activity eluting to the void volume. This was a turbid fraction containing both lipids and protein. The inhibitor activity partitioned to the organic layer of Folch extracts and was thus presumed to be a lipid. When these extracts were subjected to thin layer chromatography (TLC), more than one spot was found to contain inhibitor activity. In addition, all active spots contained phosphorous, suggesting that the inhibitor(s) was a phospholipid.

Figure 1:
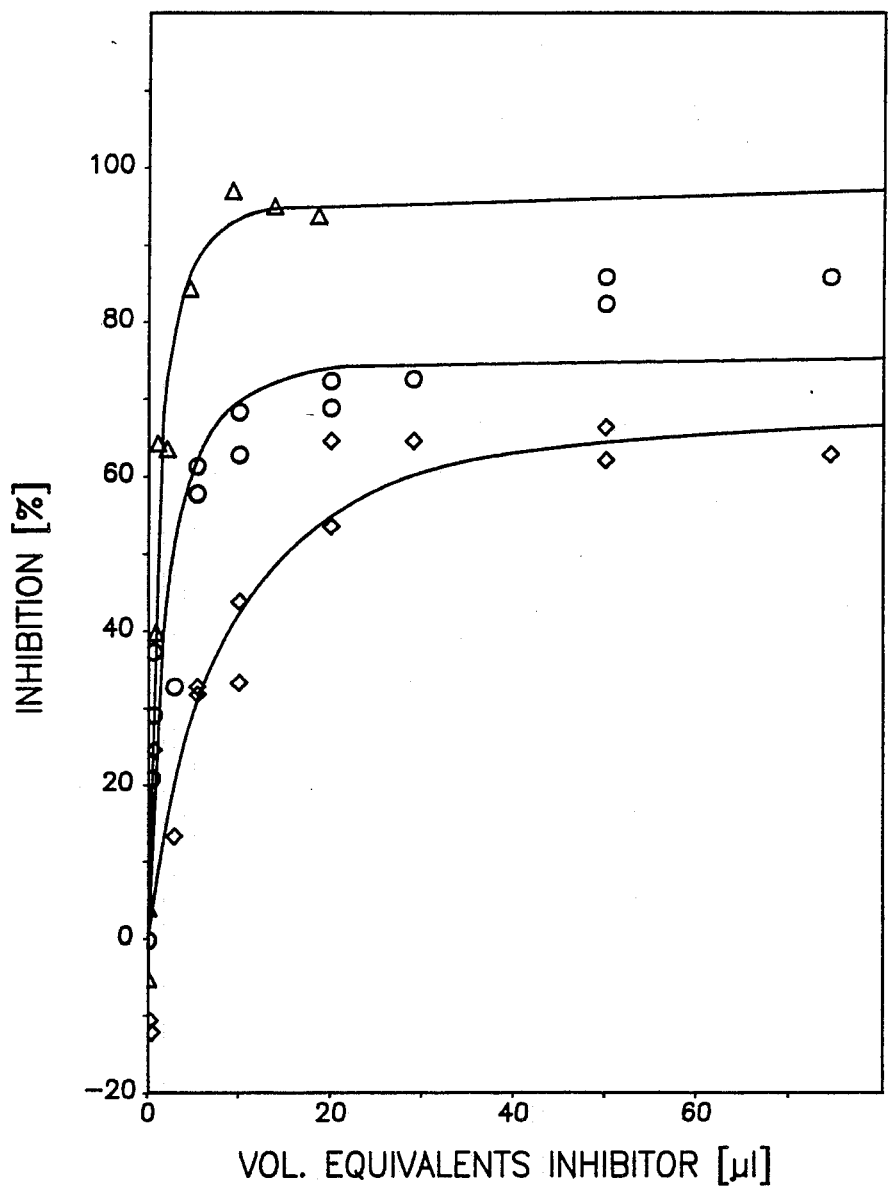
FIG. 1 is a graphic depiction of the recovery of phospholipase $A_2$ inhibitor activity in three fractions from the precedure employed to isolate one of the inhibitors of the present invention.
Figure 2:
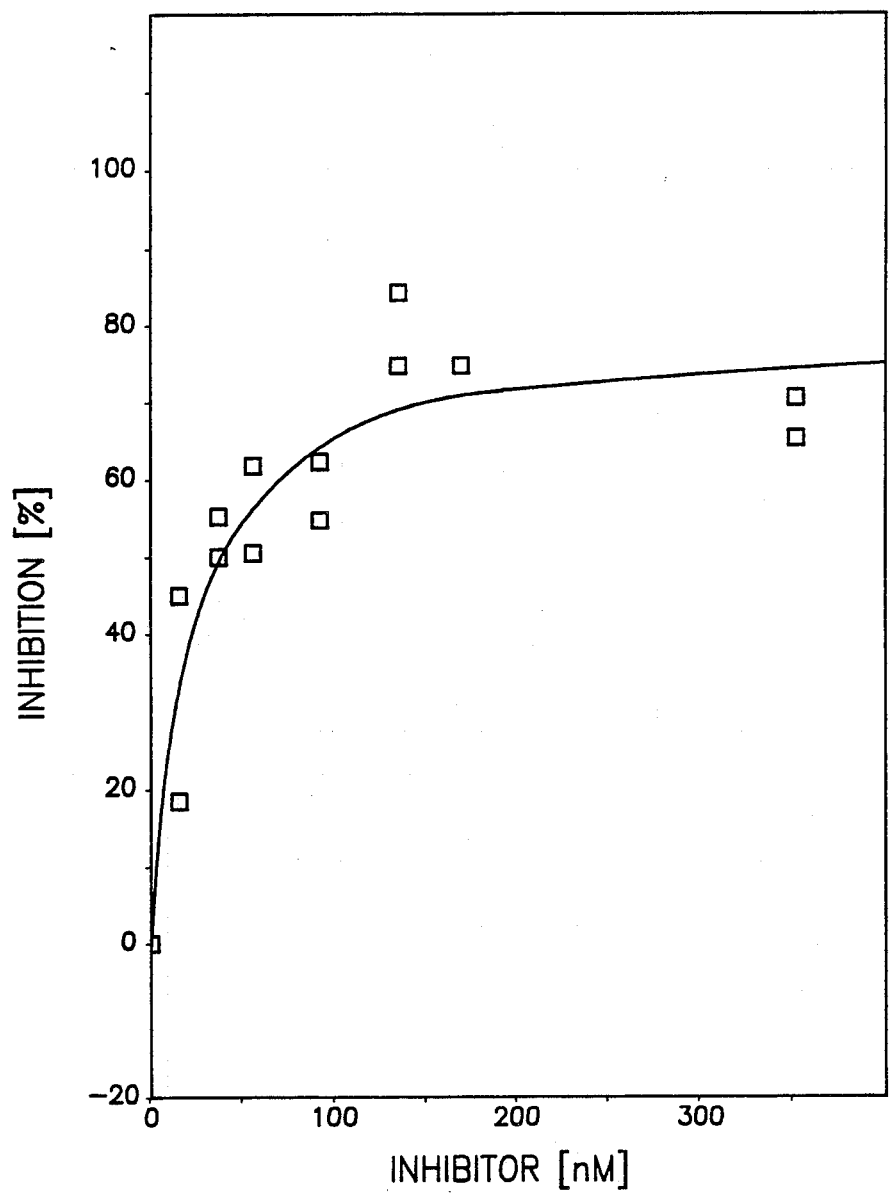
FIG. 2 is a graphic depiction of the inhibition of phospholipase $A_2$ activity by monolysocardiolipin derived from rat liver.

FIG. 1 illustrates the recovery of inhibitor activity though these steps of purification. The fractions were assayed with respect to their ability to inhibit mitochondrial phospholipase $A_2$ activity essentially by the procedure of Aarsman et al., in Biochem. Biophys. Acta., 792, 363 (1984), the disclosure of which is incorporated by reference herein. The media contained Triton X-100 (octoxynol-9) at a 1:1 mole ratio with respect to the substrate phosphatidylethanolamine. Triangular symbols (Δ) show the activity of void volume column fractions from the gel filtration column. Circular symbols (O) show the recovery of this activity in the $CHCl_3$ layer of a Folch extract. Finally, the diamond symbols ◇ show inhibitor activity eluted from a discrete spot on TLC plates on which the lipid components in the Folch extract had been separated. The spot utilized was located between phosphatidylethanolamine and cardiolipin spots when plates were prepared with silica gel H and developed with chloroform:methanol:water (65:25:4). This inhibitory component was selected for structural elucidation because its activity was higher than other components on a per lipid phosphorous basis. FIG. 2 shows the inhibitory activity of the purified component expressed on the phosphorous basis.

Subjecting the purified component to basic hydrolysis yielded phosphate, glycerol and free fatty acids in ratios of 1:1.3:1.3, respectively, on a molar basis. The composition of fatty acids obtained was determined and is summarized in Table II.

TABLE II
FATTY ACID COMPOSITION OF THE PURIFIED INHIBITORY COMPONENT

| Fatty Acid[a] | Weight[b] Percentage |
|---|---|
| Palmitic acid | 3.71 |
| Stearic acid | 1.69 |
| Oleic acid | 3.75 |
| n.i. | 6.23 |
| n.i. | 4.24 |
| Linoleic acid (18:2ω6) | 61.99 |
| n.i. | 2.54 |
| Linolenic acid (18:3ω3) | 4.27 |
| n.i. | 3.57 |
| n.i. | 3.35 |
| Ecosadienoic acid (20:2) | 2.14 |
| Ecosatrienoic acid (20:3) | 2.52 |

[a]n.i.: not identified.
[b]17:0 (heptadecanoic acid) was used as internal standard. Fatty acids isolated during the basic hydrolysis of the purified inhibitory component were converted to methyl esters and quantitated by standard GLC procedures.

Figure 3:
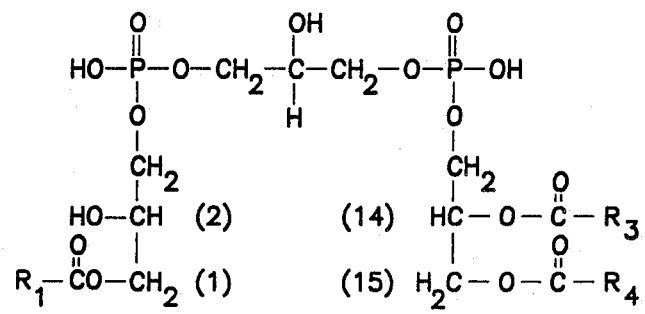
FIG. 3 depicts the structural formula of monolysocardiolipin.

The ratios of the three molecular constituents, together with the prevalence of linoleic acid (18:2) among the fatty acids indicated that the inhibitor is monolysocardiolipin. The structure of this compound is depicted in FIG. 3, wherein $R_1CO_2$, $R_3CO_2$ and $R_4CO_2$ are primarily 9, 12-octadecadienoyl residues. IR spectra of the purified inhibitor gave further evidence for this structure since they were similar to the spectrum of cardiolipin, except that the unsymmetrical band of the phosphate and hydroxyl groups at 3200 cm−1 appeared as a symmetrical band at 3380 cm−1. This alteration can be taken as an indication of the additional hydroxyl present in monolysocardiolipin.

To confirm the structure of the present inhibitor, monolysocardiolipin was prepared from bovine heart cardiolipin by treatment with snake venom (*Crotalus adamanteus*) phospholipase $A_2$, essentially as described in *Eichberg*, in J. Biol. Chem. 249, 3423 (1974), the disclosure of which is incorporated by reference herein. This material and the inhibitor purified from the acetone powder extract showed identical TLC migration behavior using several solvent systems.

Figure 4:
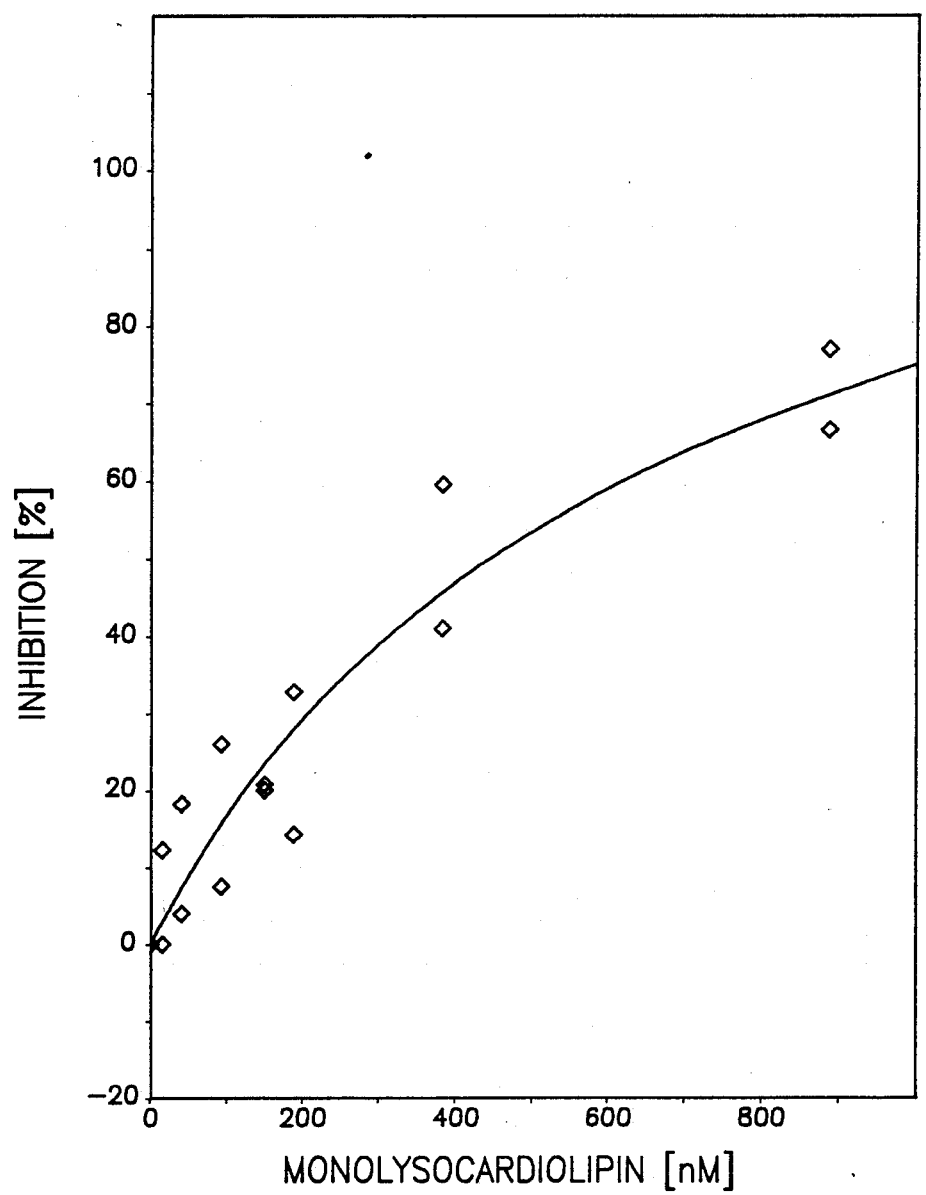
FIG. 4 is a graphic depiction of the inhibition of phospholipase $A_2$ activity by monolysocardiolipin isolated from bovine heart.

FIG. 4 shows that the monolysocardiolipin derived from bovine heart is a potent inhibitor of the mitochondrial phospholipase $A_2$.

As described hereinabove, TLC plates obtained from Folch extracts of inhibitor containing column fractions indicated the presence of more than one active species. One additional active fraction was less polar while the other was more polar than monolysocardiolipin, based on the migration behaviors observed. After identifying monolysocardiolipin, it was confirmed that the parent lipid, cardiolipin, was the less polar species while dilysocardiolipin compound was the more polar one. In FIG. 3, replacement of the $R_3CO_2$ moiety by OH would yield the structural formula of dilysocardiolipin. These inferences were confirmed by comparing the properties of two known samples of these compounds to those of the two additional inhibitory components obtained in the Folch extracts. It is probable that cardiolipin derives a substantial portion of its inhibitory activity extent by serving as a substrate for mitochondrial phospholipase $A_2$ and thereby resulting in production of the more potent mono and dilyso degradation products.

Properties of monolysocardiolipin relevant to its use as an inhibitor of phospholipase $A_2$ and therefore as a potential therapeutic agent and research tool, can be summarized as follows:

(1) The inhibitor is very potent in that 1 part in approximately 3000 (molar basis with respect to substrate) reduces mitochondrial phospholipase $A_2$ activity by 50%.

(2) The inhibitor is likely to function by a direct but noncovalent interaction with the enzyme. A direct mechanism is indicated by activity in vitro against the purified enzyme. Noncovalent interaction is indicated by loss of inhibition upon gel filtration. Absence of inhibition through an effect on the substrate's physical state is indicated by the low level at which monolysocardiolipin is active with respect to the substrate level.

(3) The high potency suggests potential high specificity and low toxicity were the agent to be used as an inhibitor in vivo.

(4) The inhibitor is a naturally occurring compound which would be subject to removal by both anabolic (reacylation) and catabolic (further hydrolysis) metabolism. No significant toxicity would exist in the products of either of these potential pathways for inhibitor metabolism.

(5) The potency of the inhibitor is expected to be adjustable by altering the position of the acyl group chains. This is indicated by the fact that monolysocardiolipin obtained from liver is more potent than that obtained from heart (compare FIGS. 2 and 4). Since cardiolipin from both liver and heart contain linoleic acid as the predominant fatty acid, it is likely that the isolated inhibitor from liver contains C-2-acyl, C-1-OH while the material synthesized enzymatically from heart cardiolipin is C-1-acyl, C-2-OH. Thus, structural isomerism is the probable cause for the difference in potency.

The method of this invention is useful both in treating a phospholipase $A_2$ mediated condition (PMC) or symptom which has already manifested itself in the mammal as well as the prevention of these conditions or symptoms in mammals particularly susceptible to them. Employment of the method of this invention prior to the development of a PMC would prevent the formation of the prostaglandins and similar products necessary for such conditions. Thus, the method of this invention can be used to prevent edema and erythema from sunburn by administering these compounds prior to exposure to sunlight. The compounds of this invention could be administered to persons suffering from hayfever or similar allergies prior to exposure to allergenic substances which are particularly hard on hayfever sufferers. In a like manner, a physician or veterinarian could readily determine other mammals or persons susceptible to a PMC.

The actual inhibition of phospholipase $A_2$ by the method of this invention takes place on a cellular level. Administration of the compound of this invention can thus be by any manner which will allow for phospholipase $A_2$ inhibition in the affected tissues or organs. The preferred route in most cases would be to systemically administer the compounds, i.e., to allow them to enter the mammal's bloodstream and thus be administered throughout the mammal's system. In certain cases, where the PMC is of a localized nature (e.g., sunburn), topical administration (e.g., transdermal) may be employed in order that the phospholipase $A_2$ inhibition is confined to the afflicted area.

Methods of administering these compounds will depend on the particular phospholipase mediated condition (PMC) sought to be treated. Regardless of the route of administration selected, the compounds used in the method of the present invention are formulated into pharmaceutically acceptable dosage forms by conventional methods known to the pharmaceutical art.

They may also be administered buccally, rectally or vaginally in forms such as suppositories. They may also be introduced parenterally, subcutaneously, or intramuscularly using sterile injectable forms known to the pharmaceutical art.

The dosage regimen for preventing or treating phospholipase mediated conditions (PMC) by the compounds of this invention is selected in accordance with a variety of factors, including the type, age, weight, sex and medical condition of the mammal, the severity of the PMC and the particular compound employed. An ordinarily skilled physician or veterinarian will readily determine and prescribe the effective amount of the anti-PMC agent to prevent or arrest the progress of the condition. In so proceeding the physician or veterinarian could employ relatively low dosages at first, subsequently increasing the dose until a maximum response is obtained.

The invention has been described with respect to various specific and preferred embodiments. However, it should be understood that many variations or modifications may be made while remaining within the spirit and scope of the invention.

What is claimed is:

1. A method for in vivo inhibition of phospholipase $A_2$ comprising administering to a mammal an effective amount of a compound of the formula;

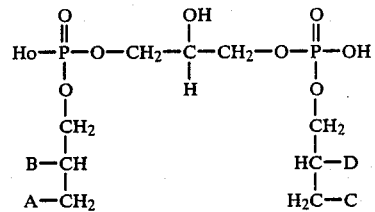

wherein A is $R_1CO_2$ OH, B is $R_2CO_2$ or OH, D is $R_3CO_2$ or OH and C is $R_4CO_2$; wherein $R_1$, $R_2$, $R_3$ and $R_4$ are each $C_{10}$-$C_{30}$ alkyl groups comprising from about 0-3 double bonds; and wherein at least A, B or D is OH.

2. The method of claim 1 wherein each of $R_1$, $R_2$, $R_3$ and $R_4$ is a $C_{12}$–$C_{22}$ alkyl group.

3. The method of claim 1 wherein B is OH, A is $R_1CO_2$ and D is $R_3CO_2$.

4. The method of claim 3 wherein the compound is monolysocardiolipin.

5. The method of claim 1 wherein A is OH, B is $R_2CO_2$ and D is $R_3CO_2$.

6. The method of claim 5 wherein the compound is isomono-lysocardiolipin.

7. The method of claim 1 wherein B is OH, A is $R_1CO_2$ and D is OH.

8. The method of claim 7 wherein the compound is dilysocardiolipin.

* * * * *